United States Patent [19]

Miwa et al.

[11] Patent Number: 4,514,502
[45] Date of Patent: Apr. 30, 1985

[54] COMPOSITE PLASMID

[75] Inventors: Kiyoshi Miwa, Matsudo; Mahito Terabe, Yokohama; Koichi Ito, Kawasaki; Masaaki Ishida, Kawasaki; Kazuhiko Matsui, Kawasaki; Shigeru Makamori, Yokohama; Konosuke Sano, Tokyo, all of Japan

[73] Assignee: Ajinomoto Co., Inc., Tokyo, Japan

[21] Appl. No.: 386,980

[22] Filed: Jun. 10, 1982

[30] Foreign Application Priority Data

May 4, 1982 [JP] Japan .................................. 57-74845

[51] Int. Cl.³ .................. C12N 1/20; C12N 15/00; C12N 1/00; C12R 1/15
[52] U.S. Cl. .................. 435/253; 435/172.3; 435/317; 435/843
[58] Field of Search ............. 435/172, 317, 253, 172.3

[56] References Cited

U.S. PATENT DOCUMENTS 4,427,773 1/1984 Tsuchida et al. ................. 435/172.3
4,430,434 2/1984 Sanders et al. ....................... 435/253

FOREIGN PATENT DOCUMENTS 0063763 11/1982 European Pat. Off. .
0063764 11/1982 European Pat. Off. .
0067564 12/1982 European Pat. Off. .

OTHER PUBLICATIONS

Gray et al., Journal of Bacteriology, vol. 145, No. 1, pp. 422-428 (Jan. 1981).
Sutcliffe et al., Genetic Engineering edited by Chakrabartz, CRC Press, pp. 83-111 (1978).
Keneko et al., Agric. Biol. Chem. vol. 43, (4), pp. 867-868 (1979).

Primary Examiner—Alvin E. Tanenholtz
Attorney, Agent, or Firm—Oblon, Fisher, Spivak, McClelland & Maier

[57] ABSTRACT

A composite plasmid which comprises (A) a drive-unit region derived from a plasmid a capable of propagating in a Coryneform glutamic acid-producing bacterium, and (B) a gene fragment derived from a plasmid b capable of propagating in *Escherichia coli* or *Bacillus subtilis* and having at least a region expressing drug resistance.

18 Claims, 8 Drawing Figures

COMPOSITE PLASMID

BACKGROUND OF THE INVENTION

1. Field of the Invention

The present invention relates to a composite plasmid, and particularly relates to a composite plasmid which is capable of propagating in Coryneform glutamic acid-producing bacteria.

2. Description of the Prior Art

Coryneform glutamic acid-producing bacteria belong to so-called "Coryneform bacteria", and are known to produce high amounts of L-glutamic acid. There are mutants of Coryneform glutamic acid-producing bacteria which produce other amino acids such as lysine; purine nucleotides such as inosine-5′-monophosphate, and other important fermentation products. Therefore, Coryneform glutamic acid-producing bacteria are of great importance to the fermentation industry.

The recently developed gene splicing techniques can successfully be applied for breeding or improving industrial microorganisms, especially in case of *Escherichia coli*. It has been difficult, however, to apply the gene splicing techniques for breeding or improving industrial microorganisms of Coryneform glutamic acid-producing bacteria, since suitable plasmid vectors useful for construction of such industrial microorganisms of Coryneform bacteria have not yet been developed.

Although several plasmids capable of propagating in Coryneform glutamic acid-producing bacteria have been found in Coryneform glutamic acid-producing bacteria, these plasmids have no inheritable characteristics which can be used as markers for easy identification. It is therefore still difficult to apply gene splicing techniques for breeding or improving industrial microorganisms of Coryneform glutamic acid-producing bacteria, even if multicopy plasmids isolated from the Coryneform glutamic acid-producing bacteria are used as the vectors.

A need, therefore, continues to exist for construction and development of a novel plasmid or vector useful for breeding or improving industrial microorganisms of Coryneform glutamic acid-producing bacteria.

SUMMARY OF THE INVENTION

It is therefore an object of the present invention to provide for a novel composite plasmid useful for breeding or improving industrial microorganisms of Coryneform glutamic acid-producing bacteria.

Another object of the present invention is to improve the characteristics of natural plasmids separated from Coryneform glutamic acid-producing bacteria to make them useful in construction of industrial microorganisms of Coryneform glutamic acid producing bacteria by gene splicing techniques.

These and other objects of the invention, as will hereinafter become more readily apparent, have been attained by providing:

A composite plasmid which comprises (A) a drive-unit region derived from a plasmid (a) capable of propagating in a Coryneform glutamic acid-producing bacterium, and (B) a gene fragment or fragments derived from a plasmid (b) capable of propagating in *Escherichia coli* or *Bacillus subtilis* and having at least a region to express resistance to a drug. When the gene fragment additionally carries a drive-unit region of plasmid (b), the composite plasmid becomes capable of propagating in *Escherichia coli* or *Bacillus subtilis*, and thus it can be screened or amplified in *Escherichia coli* or *Bacillus subtilis*.

DESCRIPTION OF THE PREFERRED EMBODIMENTS

Figure 1:
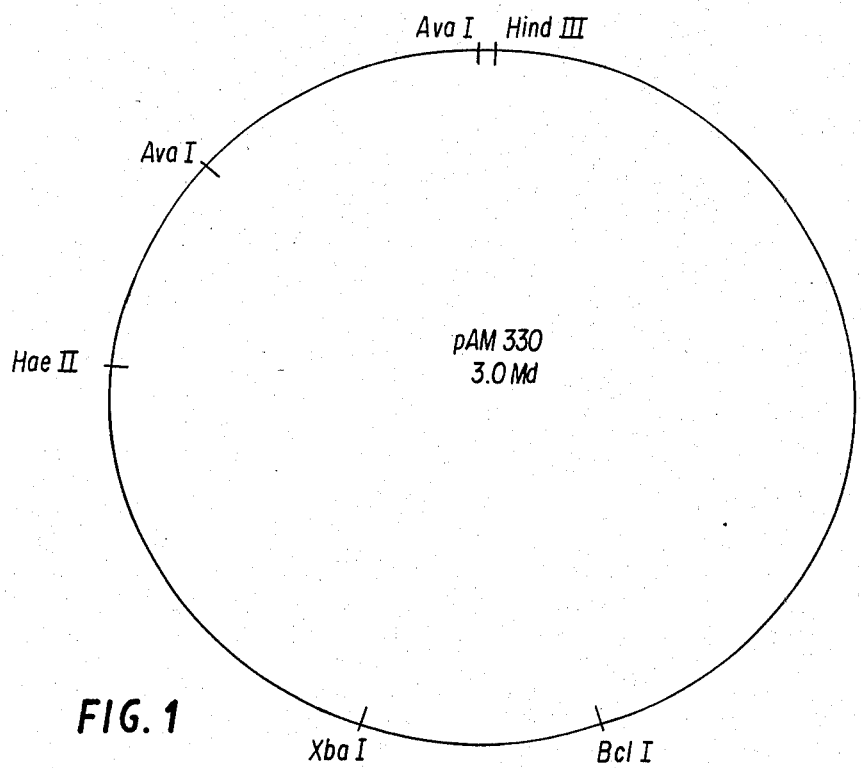
FIG. 1 shows a restriction map of plasmid pAM 330.

The term "multicopy plasmid" is used in the sense of the ordinary definition, and means a plasmid which exists in a plural number in a host cell.

"Drive-unit" is the minimum genetic region necessary for controlling the capability of gene propagation in a host cell.

"Resistance to a drug" is used in the ordinary definition and means resistance to a drug, such as an antibiotic, which inhibits the growth of a host cell. Examples of such antibiotics are penicillin, kanamycin, chloramphenicol, erythromycin, actinomycin, and the like.

Coryneform bacteria are aerobic, gram-positive rods, are non-acidfast, and are described in *Bergey's Manual of Determinative Bacteriology*, 8th ed., 599, (1974). Examples of specimens of wild strains of Coryneform glutamic acid-producing bacteria useful as hosts in this invention are as follows:

*Brevibacterium divaricatum* ATCC 14020,
*Brevibacterium saccharoliticum* ATCC 14066,
*Brevibacterium immariophilum* ATCC 14068,
*Brevibacterium lactofermentum* ATCC 13869,
*Brevibacterium roseum* ATCC 13825,
*Brevibacterium flavum* ATCC 13826,
*Brevibacterium thiogenitalis* ATCC 19240,
*Corynebacterium acetoacidophilum* ATCC 13870,
*Corynebacterium acetoglutamicum* ATCC 15806,
*Corynebacterium callunae* ATCC 15991,
*Corynebacterium glutamicum* ATCC 13032, 13060
*Corynebacterium lilium* ATCC 15990,
*Corynebacterium melassecola* ATCC 17965,
*Microbacterium ammoniaphilum* ATCC 15354.

Coryneform glutamic acid-producing bacteria also include mutants which have lost the productivity of glutamic acid or have productivity of other amino acids such as lysine and arginine; purine nucleosides such as inosine; purine nucleotides such as inosine-5′-monophosphate; and other fermentation products.

A preferred result may be obtained when the Coryneform glutamic acid-producing bacteria are mutated in a known manner to a lower restriction enzyme activity prior to using them as the hosts for the composite plasmid of the invention, or the composite plasmid having a foreign gene insertion.

When the Coryneform glutamic acid-producing bacteria as above are transformed with the composite plasmid carrying a foreign gene insert, they would then express the genetic information possessed by the foreign gene.

Specimens of multicopy plasmids capable of propagating in Coryneform glutamic acid-producing bacteria are as follows:

(1) pAM 330:
 (a) Separated from: *Brevibacterium lactofermentation* ATCC 13869.
 (b) Molecular weight: 3.0 megadalton (Calculated by migration distance on agarose gel electrophoresis and length of the DNA-chain under an electron microscope)
 (c) Sensitivity to restriction enzymes: shown in Table 1
 (d) Restriction map: shown in FIG. 1.

TABLE 1

| Restriction Enzyme | | Number of Restriction Site |
|---|---|---|
| Alu I | *Arthrobacter luteus* | ≧4 |
| Ava I | *Anabena variabilis* | ≧2 |
| Bcl I | *Bacillus caldolyticus* | 1 |
| BamH I | *Bacillus amyloliquefaciens H* | 0 |
| Bgl II | *Bacillus globigii* | 0 |
| BstE II | *Bacillus stearothermophilus ET* | ≧4 |
| EcoR I | *Escherichia coli RI+* | 0 |
| Hae II | *Haemophilus aegyptius* | 1 |
| HgiA I | *Herpetosiphon giganteus* | ≧4 |
| Hind II | *Haemophilus influenzae* | ≧4 |
| Hind III | *Haemophilus influenzae* | 1 |
| Hpa II | *Haemophilus parainfluenzae* | ≧4 |
| Kpn I | *Klebsiella pneumoniae* | 0 |
| Pvu II | *Proteus vulgaris* | 0 |
| Sac I | *Streptomyces achromogenes* | 0 |
| Sal I | *Streptomyces albus* | 0 |
| Sau 3A | *Staphylococcus aureus* | ≧4 |
| Sma I | *Serratia marcescens* | 1 |
| Sst I | *Streptomyces stanford* | 0 |
| Xba I | *Xanthomonas badrii* | 1 |
| Xho I | *Xanthomonas holicola* | 1 |
| Xma I | *Xanthomonas malvacearum* | 1 |
| Xor II | *Xanthomonas oryzae* | 0 |

(2) pAM 286:
 (a) Separated from: *Corynebacterium glutamicum* AJ 11560 (FERM-P 5485)
 (b) Molecular weight: 3.0 megadalton (Calculated by migration distance on agarose gel electrophoresis and length of the DNA-chain under an electron microscope).
 (c) Sensitivity to restriction enzymes: shown in Table 2.
 (d) Restriction map: shown in FIG. 2.

TABLE 2

| Restriction Enzyme | Number of Restriction Site |
|---|---|
| Alu I | ≧4 |
| Ava I | ≧2 |
| BamH I | 0 |
| Bcl I | 1 |
| Bgl II | 0 |
| BstE II | ≧4 |
| EcoR I | 0 |
| Hae II | 1 |
| HgiA I | ≧4 |
| Hind II | ≧4 |
| Hind III | 1 |
| Hpa II | ≧4 |
| Kpn I | 0 |
| Pvu II | 0 |
| Sac I | 0 |
| Sal I | 0 |
| Sau 3A | ≧4 |
| Sma I | 1 |
| Sst I | 0 |
| Xba I | 1 |
| Xho I | 1 |
| Xma I | 1 |
| Xor II | 0 |

(3) pHM 1519:
 (a) Separated from: *Corynebacterium glutamicum* ATCC 13058
 (b) Molecular weight: 1.8 megadalton
 (c) Sensitivity to restriction enzymes: shown in Table 3.
 (d) Restriction site map: shown in FIG. 3.

TABLE 3

| Restriction Enzyme | Number of Restriction Site |
|---|---|
| Ava I | ≧4 |
| BamH I | 0 |
| Bcl I | 1 |
| Bgl II | 1 |
| EcoR I | 1 |
| Hae II | ≧7 |
| HgiA I | ≧4 |
| Hind III | 2 |
| Kpn I | 0 |
| Sma I | 0 |
| Sac I | 2 |
| Xba I | 0 |
| Xho I | 0 |
| Xma I | 0 |

Another example of a multicopy plasmid capable of propagating in Coryneform glutamic acid-producing bacteria is reported in *Agric. Biol. Chem.*, 43, 867, (1979), which is herein incorporated by reference. The plasmid therein was separated from *Brevibacterium lactofermentum* and the molecular weight is 37 megadalton.

Plasmids (b) capable of propagating in *Escherichia coli* are preferably multicopy plamids and have genetic information of resistance to a drug. They are, for example, pAC 105, RSF 2124, pCR 1, pMB 9, pBR 313, pBR 322, pBR 324, pBR 325, pBR 327, pBR 328, pKY 2289, pKY 2700, pKN 80, pKC 7, pKB 158, pMK 2004, pACYC 177, and pACYC 184.

Plasmids (b) capable of propagating in *Bacillus subtilis* and having genetic information of resistance to a drug are preferably multicopy, such as, for example, pT 127, pC 194, pC 221, pC 223, pUB 112, pUB 110, pSA 0501, pSA 2100, pE 194, pTP 4 and pTP 5.

In order to construct the composite plasmid of the present invention from the plasmids (a) and (b), conventional methods can be employed. For example, both plasmids (a) and (b) are digested by one or several restriction enzymes which form complemental terminii, or flush end terminii at the cleaved point, and thereafter the digested plasmids (a) and (b) are ligated with a ligase.

The composite plasmid can also be prepared by cutting both plasmids (a) and (b) with one or several restriction enzymes or with shearing force, treating with an exonuclease when required, elongating to complementary single chain of oligonucleotides with terminal transferase at the terminii of the cut plasmids, and finally annealing the derivatives of the cut plasmids (a) and (b).

As to the gene fragment derived from plasmid (b) as well as plasmid (a), it is desirable to slice at a fragment thereof other than in the genetic region which expresses drug resistance, or in the genetic region which comprises the drive-unit region.

Most desirably, the gene fragment derived from plasmid (b) has both the drug resistance gene region and the drive-unit region which makes the composite plasmid a "shuttle".

After the ligation reaction, the desired composite plasmids can be screened as follows: Composite plasmids having a drive-unit region derived from plasmid (a), and a gene fragment comprising a gene region to express drug resistance derived from plasmid (b) can be obtained by isolating plasmids which can propagate in Coryneform glutamic acid-producing bacteria and can transform the Coryneform glutamic acid-producing bacteria into drug resistant. Further, a composite plasmid having a drive-unit region derived from plasmid (a), and another drive-unit region derived from plasmid (b), and the drug resistant gene of plasmid (b) can be found among plasmids which can propagate in Coryneform glutamic acid-producing bacteria and in *Escherichia coli* or *Bacillus subtilis*, and which can transform the (1) Coryneform glutamic acid-producing bacteria, or (2) *Escherichia coli*, (in case the plasmid used was capable of propagating in *Escherichia coli*) or *Bacillus subtilis*, (in case the plasmid used was capable of propagating in *Bacillus subtilis*), and which are drug resistant.

Desirable strains of *Escherichia coli* and *Bacillus subtilis* are *Escherichia coli* K-12 and *Bacillus subtilis* RM-125.

The incorporation of plasmid DNA into the hosts of Coryneform glutamic acid producing bacteria can be done by treating the cells of the DNA-recipient with calcium chloride to increase the permeability of DNA, as is reported regarding *E. coli* K-12 (Mandel, M. and Higa, A., J. Mol. Biol., 53, 159 (1970), or by incorporating at a specific a stage of growth when cells become capable of incorporating DNA (competent cells) as is reported in *Bacillus subtilis* (Duncan, C. H., Wilson, G. A. and Young, F. E., Gene 1, 153 (1977)).

The plasmid can also be incorporated into the DNA-recipient by forming protoplasts or spheroplasts of the DNA-recipient, which easily incorporate plasmid DNA, as is known in *Bacillus subtilis*, actinomycetes and yeast (Chang, S. and Choen, S. N., *Molec. Gen. Genet.*, 168, 111 (1979)); Bibb, M. J., Ward, J. M. and Hopwood, O. A., *Nature*, 274, 398 (1978); Hinnen, A., Hicks, J. B. and Fink, G. R., *Proc. Nat'l. Acad. Sci. USA.* 75, 1929 (1978)).

Since the composite plasmid obtained in this invention can transform Coryneform glutamic acid-producing bacteria into drug resistant bacteria, Coryneform glutamic acid-producing bacteria which contain the composite plasmid or composite plasmid inserted with a foreign gene can be easily identified by testing their resistance to the drug.

When the composite plasmid possesses a gene fragment having a drive-unit region of plasmid (b), the composite plasmid can also propagate in *Escherichia coli* or *Bacillus subtilis*, and the composite plasmid or a composite plasmid carrying a foreign gene insertion can be amplified or cloned using *Escherichia coli* or *Bacillus subtilis*.

The composite plasmids of the present invention contained in the hosts are deposited at selected International Depositary Authorities as follows:

pAJ 655: *Escherichia coli* AJ 11882, FERM-P 6517=FERM-BP 136 *Corynebacterium glutamicum SR* 8201 ATCC 39135 pAJ 611: *Escherichia coli* AJ 11884 FERM-P 6519=FERM-BP 138 pAJ 1844: *Escherichia coli* AJ 11883 *Corynebacterium glutamicum SR*8202 ATCC 39136 pAJ 440: *Bacillus subtilis* AJ 11901 FERM-BP 140 pAJ 3148: *Corynebacterium glutamicum SR*8203 ATCC 39137

The composite plasmid of the present invention can be obtained from the cells of the microorganisms deposited in the International Depositary Authorities by lysing the cells previously harvested at a late exponential growth phase with lysozyme and SDS, adding polyethylene glycol to a supernatant obtained from the lysate by centrifugation at 30,000 Xg, and purifying the precipitated DNA by fractionation using cesium chlorideethidium bromide equilibrium density gradient centrifugation.

The composite plasmid in the host strain can be expelled to obtain host strain without injury thereto from the deposited microorganism as follows: The plasmid may be lost spontaneously from hosts or can be eliminated by a "curing" treatment [*Bact. Rev.*, 36, p 361-405 (1972)]. An example of curing is as follows: A small inoculum of about $10^4$ cells/ml of the strain is cultured overnight at 27~35° C. in a medium containing a subinhibitory concentration (2-50 $\mu$g/ml) of acridine orange to give incomplete inhibition of growth [*J. Bacteriol.*, 88, 261 (1964)]. The culture is plated on an agar plate, and incubated at 27~42° C. overnight. Many of the colonies appearing on the plate may quite likely be cured of plasmid.

Having now generally described this invention, the same will become better understood by reference to certain specific examples which are included herein for purposes of illustration only and are not intended to be limiting unless otherwise specified.

EXAMPLE 1

In the present Example is shown a composite plasmid, pAJ 655 which was constructed from plasmids pBR325 and pAM 330, which composite plasmid can multiply in *Escherichia coli* K-12.

(1) Plasmid pBR 325 is a plasmid of 3.6 Md originating *Escherichia coli*; it confers resistance to tetracycline, chloramphenicol, and ampicillin in *Escherichia coli* [Boliver, F. Gene, 4, 121 (1978)]. The sample of pBR 325 used in this example was purchased from Bethesda Research Laboratory (BRL).

(2) Plasmid pAM 330 is a plasmid of 3.0 Md newly isolated by the inventors from *Brevibacterium lactofermentum* ATCC 13869, and the restriction map of the plasmid is shown in FIG. 1.

A sample of the plasmid pAM 330 DNA was prepared as follows: Cells of *Brevibacterium lactofermentum* ATCC 13869 were harvested by centrifugation at late exponential growth phase at 30° C. in 1 liter of CMG medium, pH 7.2, which contained, per liter of distilled water: 10 g peptone, 10 g yeast extract, 5 g NaCl, and 5 g glucose. The cells obtained were lysed by a conventional method such as treatment with lysozyme and sodium dodecyl sulfate. Supernatant (64 ml) of the lysate was obtained by centrifugation at 30,000 xg for 30 minutes, and the DNA in the supernatant was precipitated by the addition of polyethyleneglycol (final 10%), and resolved in 10 ml of TEN buffer. After an RNase treatment (50 μg/ml of RNase I at 37° for 30 minutes) and phenol extraction, DNA was precipitated with 2 volumes of ethanol at 31 20° C. and resolved in 1 ml of TEN buffer. The DNA obtained was applied to agarose gel electrophoresis. About 74 μg of the plasmid DNA was isolated from the gels.

(3) Construction, isolation and identification of composite plasmids.

(i) Plasmid pBR 325 DNA (0.2 μg) was digested with 1 unit of restriction enzyme BamHI (purchased from BRL) at 37° C. for 60 minutes.

(ii) pAM 330 DNA (1.2 μg) was partially digested at 37° C. for 15 minutes with 0.2 unit of restriction enzyme MboI.

(iii) Digested DNAs obtained in (i) and (ii) were mixed and kept at 65° C. for 10 minutes, followed by a ligation reaction with 0.01 unit of T4 DNA ligase in the presence of ATP and dithiothreitol at 22° C. for 2 hours. The reaction mixture was heated at 65° C. for 10 minutes, mixed with 2 volumes of ethanol, and thereafter the ligated DNA fractions were collected by centrifugation at 15,000 xg for 15 minutes. Composite plasmid DNA thus obtained was used in the following transformation (iv).

(iv) Cells of a middle logarithmic phase of *Escherichia coli* C-600 (thr$^-$, leu$^-$, thiamine$^-$, r$^-$,$^m$$^-$) (Meselson, M. and Yuan, R. Nature, 217, 1110 (1968) were obtained by cultivation at 30° C. in 20 ml of CGM medium. The cells of C-600 were transformed with the DNA obtained in (iii) according to the method in Kushner, et al., "Genetic Engineering", p. 17 (1978), Elsevier/North Holland Biomedical Press.

Transformants were selected using CMG agar plates supplemented with 20 μg/ml of chloramphenicol after having been cultivated at 37° C. for 24 hours. Among these transformants, strain AJ 11882 was selected and used for further examinations.

The DNA of the composite plasmid, named pAJ 655, was isolated from the cell lysate of AJ 11882 by the following method: Cells of AJ 11882 were obtained after culture in CMG medium and lysed by a conventional method [Tanaka et al., *J. Bacteriol.*, 121, 354 (1975)], and the lysate was applied to agarose gel and electrophoresed [Sharp et al., *Biochemistry* 12, 3055 (2973)]. By comparing to the molecular weight standards (pBR 325) the Molecular Weight of the plasmid was determined as 6.6 Md.

Figure 4:
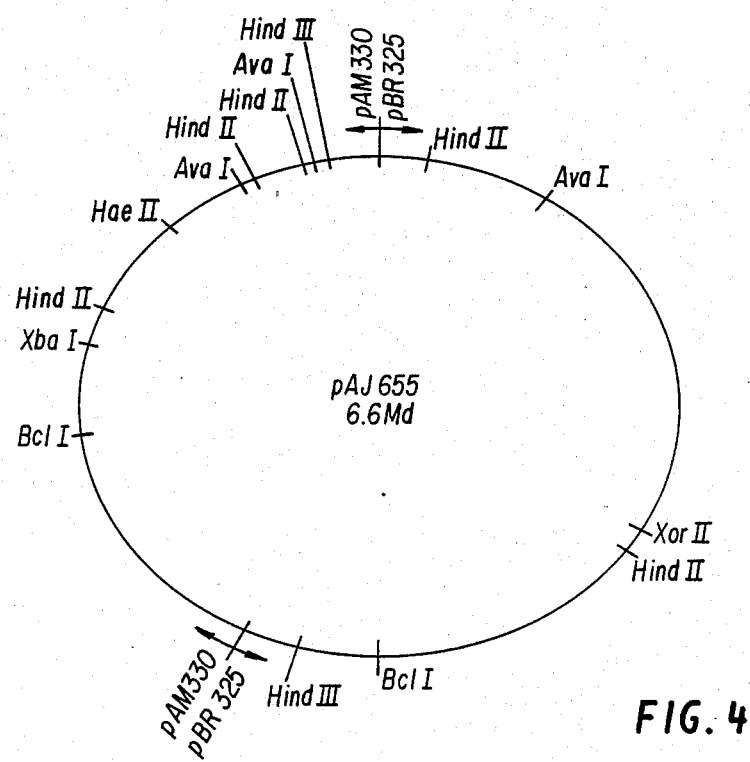
FIG. 4 shows a restriction map of composite plasmid pAJ 655.

The restriction map of the plasmid, illustrated in FIG. 4, shows that the plasmid is composed of fragments of pBR 325 and pAM 330, as determined the method of K. J. Danna in Methods in Enzymology 65, 449 Academic Press (1980).

EXAMPLE 2

In the present Example it is shown that the composite plasmid, pAJ 655 obtained in Example 1 can multiply in *Brevibacterium lactofermentum* and an antibiotic resistance marker on pAJ 655 originated from pBR 325 is expressed.

The recipient strain used was *Brevibacterium lactofermentum No.* 64 which was a triple (lysine, methionine and threonine) auxotrophic mutant derived from *Brevibacterium lactofermentum* ATCC 13869.

(1) Preparation of protoplast. *Brevibacterium lactofermentum* No. 64 ATCC No. 39134 was cultured in 5 ml of CMG medium until at an early exponential growth phase, 0.6 ml units of penicillin G was added and the cultivation was continued further for 1.5 hours. Cells were collected by centrifugation and washed with 0.5 ml of SMMP medium composed of 0.5M sucrose, 20 mM maleic acid, 20 mM MgCl$_2$, 3.5% "Pennassay broth" (Difco), pH 6.5. Protoplasts were prepared from these cells by treatment with 10 mg/ml lysozyme in SMMP medium at 30° C. for 20 hours (followed by centrifugation 6,000 xg for 10 minutes.), washed with SMMP medium and resuspended in 0.5 ml SMMP.

(2) Transformation, selection of transformant and identification of plasmid. Protoplasts thus obtained in (1) were mixed with 2 μg of pAJ 655 DNA prepared in Example 1 in 0.1 ml, and added to final 30% polyethyleneglycol and kept at room temperature for 2 minutes in order to absorb and introduce the DNA into the protoplasts. After having been washed in 1 ml of SMMP medium the protoplasts with DNA were resuspended in 1 ml of SMMP medium, and cultured at 30° C. for 3 hours for the expression of drug resistance. The resulting culture liquid was spread onto a "protoplast regeneration medium", pH 7.0, which contained, per one liter of distilled water: 12 g Tris(hydroxymethyl)aminomethane, 0.5 g KCl, 10 g glucose, 8.1 g MgCl$_2$.6H$_2$O, 2.2 g CaCl$_2$.2H$_2$O, 4 g peptone, 4 g yeast extract, 1 g "Casamino acid" (Difco), 0.2 g K$_2$HPO$_4$, 135 g Na-succinate, 18 g agar and 5 μg/ml chloramphenicol. Five of the colonies which appeared after 3–10 days cultivation, at 30° C., were further examined by culturing on CMG medium supplemented with 20 μg of chloramphenicol per ml and the cells resistant to chloramphenicol was lysed to detect the existence of plasmid. The lysates were applied to agarose gel and electrophoresed by the same methods as in Example 1 and found having plasmids of the same molecular weight and the same restriction map as pAJ 655.

EXAMPLE 3

In the present Example, it is shown that the composite plamid pAJ611 made in Example 4 can multiply in *Corynebacterium glutamicum* and express the antibiotic resistance marker originated from pBR325.

*Corynebacterium glutamicum* ATCC 13060 was used as the recipient strain, and its protoplast transformation with pAJ611 DNA extracted from *Escherichia coli* AJ 11884 was carried out as described in Example 2.

One of the transformants named as SR-8201, was resistant to Chloramphenicol in CMG, and contained the same plasmid as pAJ611 as determined from the molecular weight and the restriction map.

EXAMPLE 4

In the present Example is shown a composite plasmid, named pAJ 611, which was constructed from plasmid pBR 325 and plasmid pAM 286, and it is shown that the composite plasmid can multiply in *Escherichia coli*.

(1) Plasmid pBR 325 used was the same sample as in Example 1.

Figure 2:
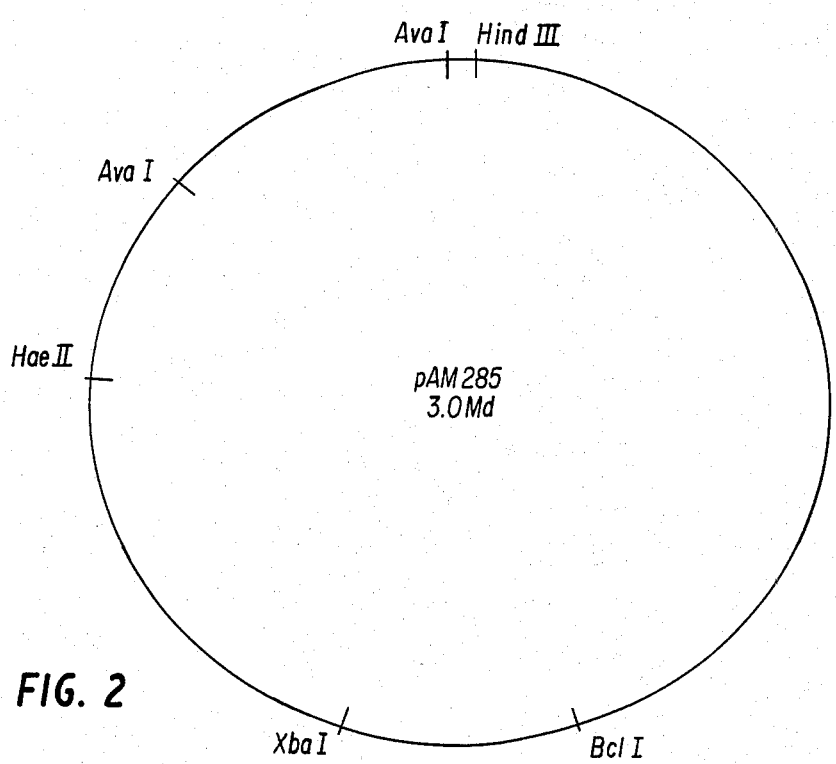
FIG. 2 shows a restriction map of plasmid pAM 286.

(2) Plasmid pAM 286 is a plasmid newly isolated by the inventors from *Corynebacterium glutamicum* AJ 11560 (deposited as FERM-P 5485). Its molecular weight is 3.0 Md and its restriction map is shown in FIG. 2. About 20 μg of plasmid pAM 286 was obtained by the same procedure in Example 1.

Figure 5:
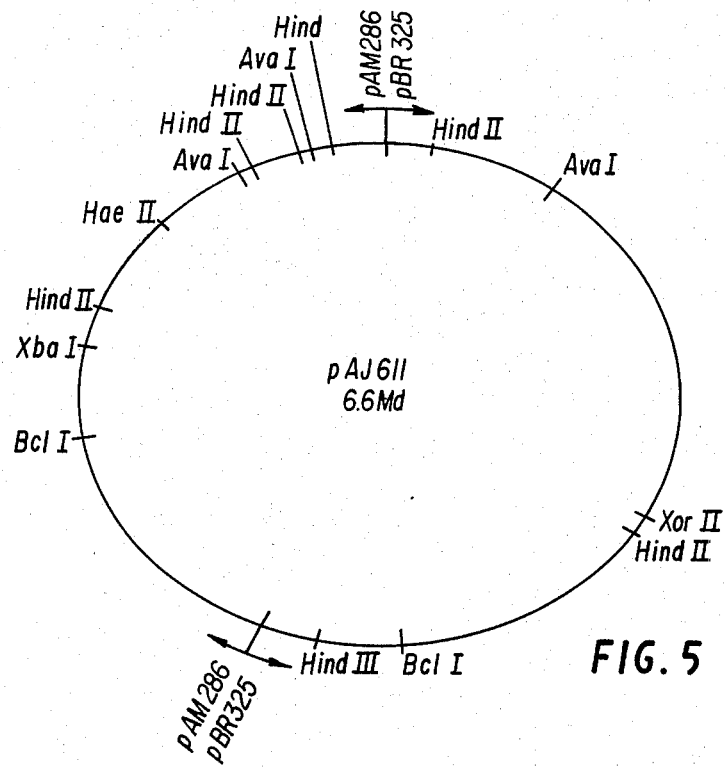
FIG. 5 shows a restriction map of composite plasmid pAJ 611.

(3) Construction, isolation and identification of composite plasmid pAJ 611 was carried out by the method of Example 1 except pAM 286 DNA was used in place of pAM 330 DNA. The composite plasmid pAJ 611, whose molecular weight was 6.6 Md and whose restriction map is shown in FIG. 5, was screened using *Escher-* ichia coli C-600 as the host by the same procedure as in Example 1, pAJ 611 was obtained by the manner shown in Example 1 from *Escherichia coli*, AJ 11884, harbouring pAJ 611.

EXAMPLE 5

In the present Example is shown a composite plasmid, pAJ 440, which was constructed from plasmid pUB 110 and pAM 330, and it is shown that the composite plasmid can multiply in *B. substilis.*

(1) Plasmid pUB 110 is a plasmid of 3.0 Md. originating in *Staphylococcus aureus,* it replicates and confers resistance to kanamycin in *Bacillus subtilis* [Keggins, K, M, Lovett, P, S, and Duval, E. J., Proc, Natl, Acad, Sci., 75, 1423 (1978)]. The sample of pUB 110 used was purchased from Bethesda Research Laboratory (BRL) and used according to the direction of the maker.

(2) Preparation of plasmid pAM 330 is described in Example 1.

(3) Construction, isolation and identification of composite plasmids.

(i) pUB 110 DNA(0.2 µg) was digested at 37° C. for 60 minutes with 1 unit of restriction enzyme Bam HI (purchased from BRL)

(ii) pAM 330 DNA (1.2 µg) was partially digested at 37° C. for 15 minutes with 0.2 unit of restriction enzyme MboI.

(iii) Digested DNAs (i) and (ii) were mixed, ligated by the method described in Example 1, and the ligated DNA was electrophoresed using 0.8% agarose gel at 5 v/cm for 2 hours in Tris-acetate buffer (pH 8.0) system. The DNA fraction which ran slower than pUB 110 monomer DNA was extracted from the gel, treated with phenol, and collected as ethanol precipitate.

(iv) *Bacillus subtilis* RM 125 (arg-, leu-, r-, m-) [Uozumi, T. et. al., Molec. Gen. Genet, 152, 65 (1975)] was transformed with the DNA mixture obtained in (iii) according to a conventional procedure [Dabnau, D., et al., J. Mol. Biol., 56, 209 (1971)]. Transformants were selected using CMG agar plates supplemented with 5 µg/ml kanamycin as those which propagated by cultivation at 37° C. for 24 hours.

Figure 7:
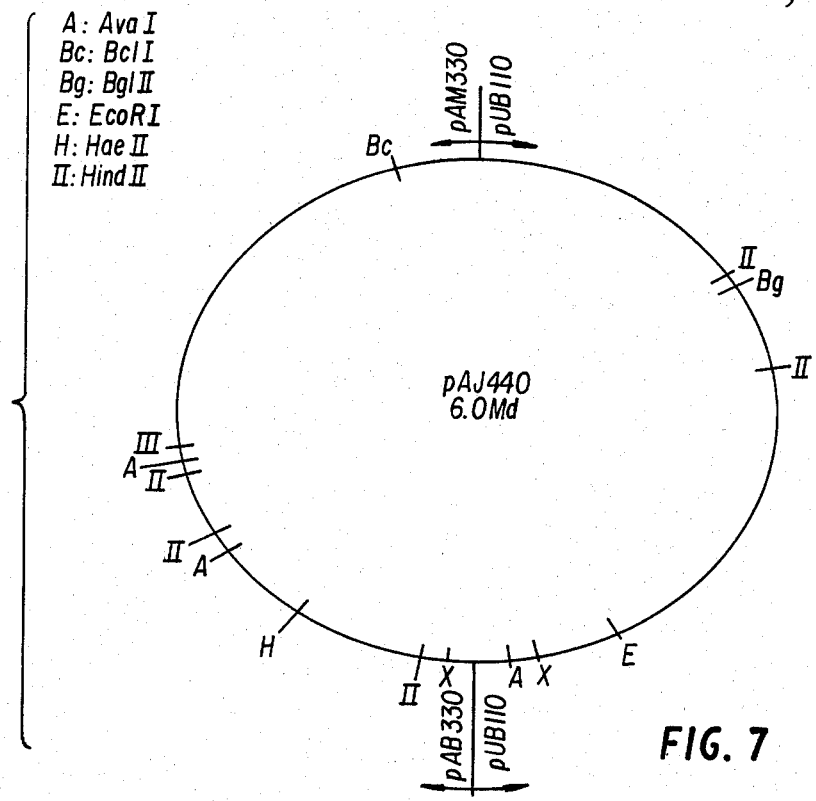
FIG. 7 shows a restriction map of composite plasmid pAJ 440.

Twenty transformants appearing on the CMG agar plates supplemented with 5 µg/ml kanamycin were lysed, and plasmid DNA was detected. One of them which had a clear plasmid band was designated as KS 440, deposited at ATCC No. 39139 and the plasmid was named pAJ 440. The pAJ 440 DNA was extracted from the gel, and cleaved by several restriction enzymes. This plasmid pAJ 440 was concluded to be a composite plasmid of pUB 110 and pAM 330, according to the molecular weight of 6.0 Md and the restriction map, which is shown in FIG. 7.

EXAMPLE 6

In the present Example is shown that the composite plasmid pAJ 440 can multiply in *Brevibacterium lactofermentum,* and that an antibiotic resistance marker on pAJ 440 originated from pUB 110 is expressed.

The host strain used was *Brevibacterium lactofermentum* No. 64. Protoplast transformation of No. 64 with pAJ 440 DNA was carried out by the method described in Example 2 with the following exceptions: 1 µg of pAJ 440 DNA was used for transformation, and the "Protoplast regeneration medium" containing 100 µg/ml of kanamycin was used for the selection of transformants.

Two of the transformants which appeared after 3-10 days cultivation, were cultured on CMG medium supplemented with 20 µg/ml kanamycin, lysed, and the lysate was applied to agarose gel and electrophoresed for the detection of plasmids by the same methods as in the previous Examples. Plasmids of the molecular weight and of the same restriction map of pAJ 440 in Example 4 were found in both transformants.

EXAMPLE 7

In the present Example is shown a composite plasmid, pAJ 1844 which was constructed from plasmid pBR 325 and pHM 1519; the composite plasmid can multiply in *Escherichia coli.*

(1) Plasmid pBR 325 used was the same sample shown in Example 1.

Figure 3:
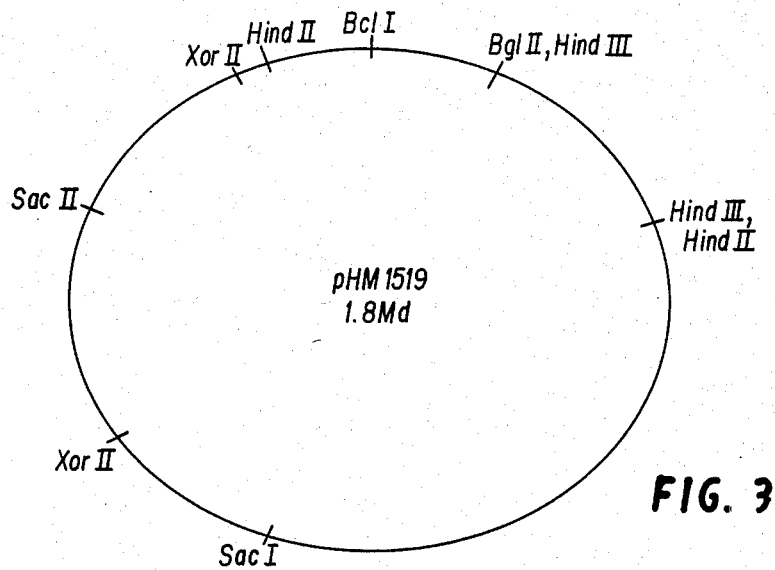
FIG. 3 shows a restriction map of plasmid pHM 1519.

(2) Plasmid pHM 1519 is a plasmid newly isolated by the inventors from *Corynebacterium glutamicum* ATCC 13058. Its molecular weight is 1.8 Md and its restriction map is shown in FIG. 3. About 24 µg of pHM 1519 DNA was obtained by the same procedure as in Example 1.

(3) Construction, isolation and identification of the composite plasmid pAJ 1844.

(i) 0.2 µg of pBR 325 DNA was digested by the method of Example 1.

(ii) 1.0 µg of plasmid pHM 1519 DNA was digested with 5 units of a restriction enzyme Bgl II (Boehringer Manheim GmbH) at 37° C. for 60 minutes.

Figure 6:
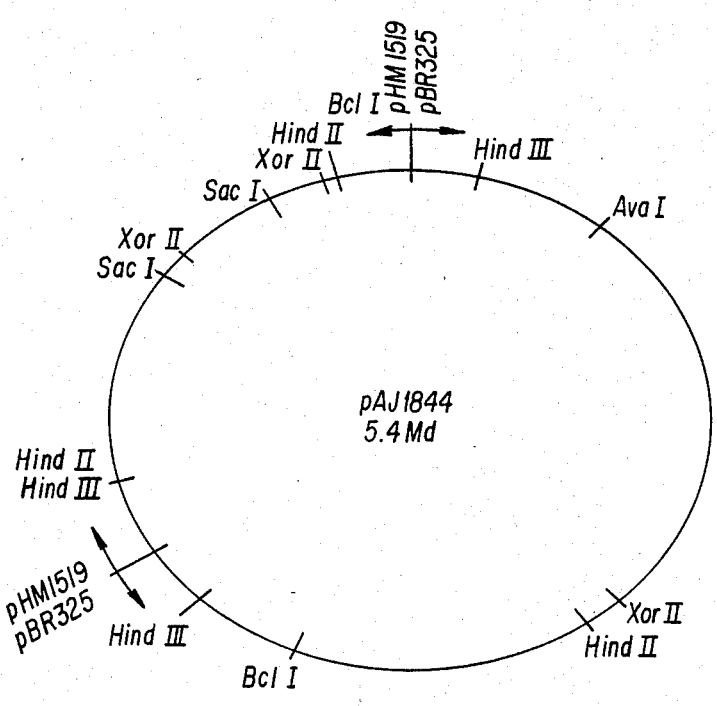
FIG. 6 shows a restriction map of composite plasmid pAJ 1844.

(iii) Transformants were obtained by introducing composite plasmid DNA into *Escherichia coli* C-600 by the procedure shown in Example 1. A composite plasmid, named pAJ 1844, was isolated from one of the transformants i.e., *Escherichia coli* AJ 11883. Its molecular weight is 5.4 Md and its restriction map is shown in FIG. 6.

EXAMPLE 8

In the present Example, it is shown that the composite plasmid pAJ 1844 constructed in Example 7 can propagate in *Corynebacterium glutamium and express the antibiotic resistance markers on pAJ* 1844 originated from pBR 325.

*Corynebacterium glutamicum* ATCC 13032 was used as the recipient and by the protoplast transformation system described in Example 2, pAJ1844 DNA obtained from *Escherichia coli* AJ11883 was successfully introduced and confirmed as the same plasmid as pAJ1884. SR-8202 is a representative transformant harboring pAJ1844.

EXAMPLE 9

In the present Example is shown a composite plasmid, named pAJ 3148, which was constructed from plasmids pUB 110 and pHM 1519; the composite plasmid can multiply in *Bacillus subtilis.*

(1) Plasmid pUB 110 used was the same sample as in Example 5, and digested with restriction enzyme Bam HI by the method of Example 5.

(2) Plasmid pHM 1519 used was the same sample, and digested with restriction enzyme Bgl II by the method of Example 7.

Figure 8:
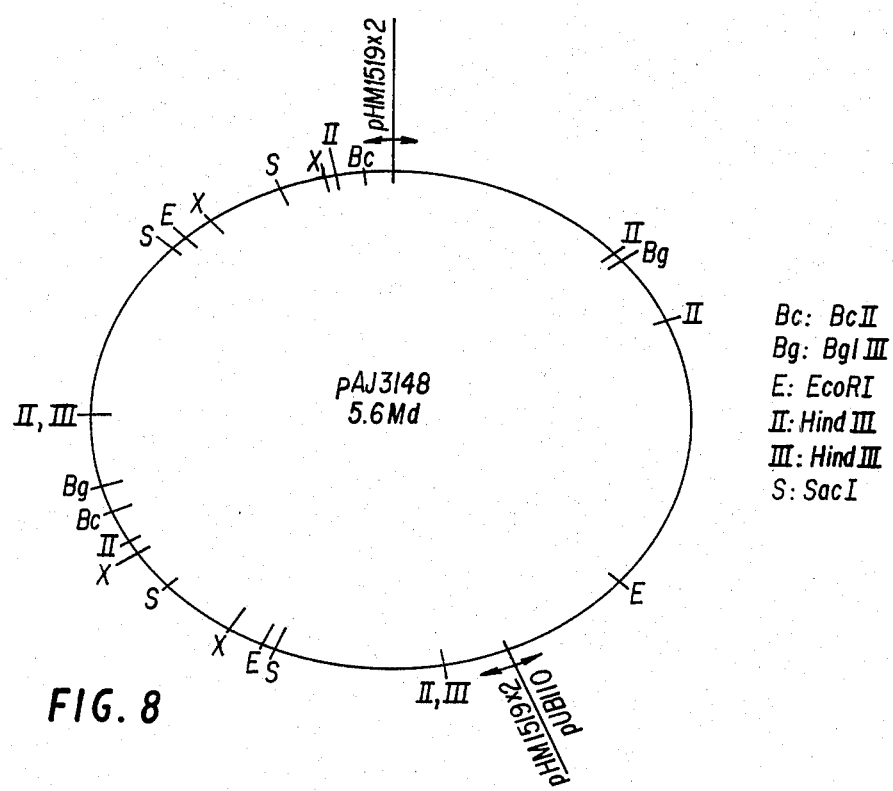
FIG. 8 shows a restriction map of composite plasmid pAJ 3148.

(3) Digested DNAs obtained in (1) and (2) were mixed, and ligated, and the ligated DNA was electrophoresed. DNA larger than pUB 110 monomer was isolated, and introduced into *Bacillus subtilis* RM 125, by the method of Example 5. A plasmid larger than pUB 110 was detected in a transformant designated as No. 1129. This plasmid, pAJ 3148, was shown to have a molecular weight of 6.6 Md and its restriction map is shown in FIG. 8. As shown in FIG. 8, this plasmid is composed of 1 molecule of pUB 110 and two molecules of pHM 1519.

EXAMPLE 10

In the present Example, it is shown that the composite plasmid pAJ3148 constructed in Example 9 can propagate in *Corynebacterium glutamicum* and express the antibiotic resistance marker originated from pUB110.

*Corynebacterium glutamicum* ATCC 13032 was used as the recipient, and by the protoplast transformation system described in Example 2, pAJ3148 DNA obtained from *Bacillus Subtilis* No. 1129 was able to be introduced into ATCC 13032, propagated, and expressed kanamycin resistance. The molecular weight and the restriction map were the same as those of pAJ3148.

EXAMPLE 11

In the present Example is shown a model of a cloning experiment. A new composite plasmid pSR8204 was constructed from the vector plasmid pAJ1844 described in Example 7 and a chromosomal DNA fragment which carries at least one gene for m-fluoro-phenylalanine resistance.

(1) Plasmid pAJ1844 is a composite plasmid constructed in Example 7 and propagated in *Escherichia coli* AJ 11883 described in Example 7. pAJ1844 was used as a vector and digested by Pst I restriction enzyme.

(2) As a model of inserted DNA fragment, the chromosomal DNA of *Brevibacterium lactofermentum* FERM p-1914 was chosen, extracted, and cut by Pst I. FERM p-1914 is characterized by its m-fluoro-phenylalanine resistance, and productivity of phenylalamine in the medium.

(3) Both Pst I digested DNA's, vector plasmid and chromosomal DNA were mixed and ligated.

(4) Ligated DNA was challenged to the protoplast of *Corynebacterium glutamicum* (ATCC 13060) and the transformants were first selected as the chloramphenicol resistant. A second screening was to check the resistancy to m-fluoro-phenyl-alanine; the third was the productivity of phenylalanine. Plasmid DNA analysis on a cleaved lysate of transformant was done by agarose gel electrophoresis.

EXPERIMENTAL (i) Vector DNA: Composite plasmid pAJ1844 was extracted from *Escherichia coli* AJ 11883. To 20 ml CMG culture of AJ 11883, at late logarithmic growing phase, was added 170 µg/ml of chloramphenicol and then cultivated an extra 18 hr. TENµg of plasmid DNA was obtained from the cleared lysate of chloramphenicol treated cells. 0.05 µg of this DNA was completely digested by Pst I for 60 min. at 37° C., and the aliquots were combined.

(ii) Chromosomal DNA: 30 mg of chromosomal DNA of *Brevibacterium lactofermentum* AJ 3437 (FERM p-1914) was extracted from 1 l of CMG culture by a conventional phenol method. 10 µg of this DNA was partially digested by 10 units of Pst I for 5 minutes to 60 minutes at 37° C., and aliquots were accumulated.

(iii) Ligation: DNA's (i) and (ii) were mixed and ligated by 0.1 unit of T4 ligase for 4 hr. at 22° C. Other conditions were the same as in Example 1.

(iv) Recipient cells: Protoplasts of *Corynebacterium glutamicum* ATCC 13060 were used as the recipient for the ligated DNA (iii). To prepare the protoplast, early exponentially growing cells in CMG medium were treated by 1.2 unit/ml of penicillin G for 1.5 hr., harvested, washed, resuspended in 0.5 ml of SMMP medium which contained 10 mg of egg-white lysozyme and incubated for 20 hr. at 30° C.

(v) Transformation: ligated DNA (iii) and protoplast (iv) were combined and adsorption of DNA to the protoplast was stimulated by the addition of polyethylene glycol (final 30%). The DNA-protoplast complex thus obtained was washed and plated on the regeneration medium (Example 2) which contains 5 µg/ml of chloramphenicol as a selection drug.

(vi) Transformant: Several hundreds of chloramphenicol resistant transformants were picked up and examined for m-fluoro-phenylalamine resistancy to 1 mg/ml of m-fluoro-phenylamine in the minimal medium which contained, per one liter of distilled water, 10 g glucose, 2 g$(NH_4)_2SO_4$, 1 g $KH_2PO_4$ 0.4 g $MgSO_4$, $7H_2O$, 2 ppm $Fe^{++}$, 2 ppm $Mn^{++}$, 100 µg d-biotin, 1 mg thiamine HCl, 15 g agar, at pH 7.2.

(vii) Plasmid analysis: Cleared lysate of transformants were applied to agarose gel with molecular weight standards (pAJ 1844 and pAJ 655) and electrophresed. The molecular weight of plasmid in a transformant was about 6 megadalton.

This transformant was designated as SR 8204, ATCC39138 and harboring plasmid pSR8204.

(viii) Production of phenylalanine: The amounts of phenylalamine produced in medium-P were 1 g/l by SR8204 and lower than 0.1 g/l by host ATCC 13060. Those of tyrosine produced in the same medium were 0.4 g/l by SR 8204 and lower than 0.1 g/l by host ATCC 13060. The medium-P contained in 1 l distilled water, 100 g glucose, 40 g$(NH_4)_2SO_4$, 1 g $KH_2PO_4$, 0.4 g $MgSO_4.7H_2O$, 2 ppm $Fe^{++}$, 2 ppm $Mn^{++}$, 100 µd-biotin, 1 mg thiamine HCl, 50 g $CaCO_3$, pH 7.0.

All strains deposited at the ATCC (SR-8201, SR-8202, SR-8203, SR-8204, Brevibacterium No. 64 and KS 440) were deposited on June 3, 1982.

Having now fully described this invention, it will be understood by those of skill in the art that the same can be performed within a wide and equivalent range of conditions, parameters and the like without affecting the spirit or scope of the invention or of any embodiment thereof.

What is claimed as new and desired to be secured by Letters Patent of the United States is:

1. A composite plasmid which comprises
(A) a minimum genetic region, necessary for controlling the capability of gene propagation in a *Coryneform glutamic* acid-producing bacterium, derived from a plasmid (a) selected from the group consisting of pAM 330, pAM 286 and pHM 1519, and
(B) a gene fragment derived from a plasmid (b) capable of propagating in *Escherichia coli* or *Bacillus*

*subtilis* having at least a region expressing drug resistance.

2. The composite plasmid of claim 1, wherein said gene fragment derived from the plasmid (b) further has a minimum genetic region necessary for controlling the capability of gene propagation in *E. coli* or *B. subtilis*.

3. The composite plasmid of any of claims 1 or 2, wherein said plasmid (b) is pT 127, pC 194, pC 221, pC 223, pUB 112, pUB 110, pSA 0501, pSA 2100, pE 194, pTP 4 or pTP 5.

4. The composite plasmid of any of claims 1 or 2, wherein said plasmid (b) is pAC 105, RSF 2124, pCR1, pMB 9, pBR 313, pBR 322, pBR 324, pBR 325, pBR 327, pBR 328, pKY 2289, pKY 2700, pKN 80, pKC 7, pKB 158, pMK 2004, pACYC 177, or pACYC 184.

5. The composite plasmid of any of claims 1 or 2, wherein said *Coryneform glutamic* acid producing bacterium is

*Microbacterium ammoniaphilum,*
*Bevibacterium divaricatum,*
*Brevibacterium saccharoliticum,*
*Brevibacterium immariophilum,*
*Brevibacterium lactofermentum,*
*Brevibacterium roseum,*
*Brevibacterium flavum,*
*Brevibacterium thiogenitalis,*
*Corynebacterium acetoglutamicum,*
*Corynebacterium callunae,*
*Corynebacterium glutamicum,*
*Corynebacterium lilium,* or
*Corynebacterium melassecola.*

6. The composite plasmid of any of claims 1 or 2, wherein said *Cornyeform glutamic* acid-producing bacterium is

*Brevibacterium divaricatum* ATCC 14020,
*Brevibacterium saccharoliticum* ATCC 14066,
*Brevibacterium immariophilum* ATCC 14068,
*Brevibacterium lactofermentum* ATCC 13869,
*Brevibactrium roseum* ATCC 13825,
*Brevibacterium flavum* ATCC 13826,
*Brevibacterium thiogenitalis* ATCC 19240,
*Corynebacterium acetoacidophilum* ATCC 15806,
*Corynebacterium callunae* ATCC 15991,
*Corynebacterium glutamicum* ATCC 13032, 13060,
*Corynebacterium lilium* ATCC 1599 or
*Corynebacterium melassecola* ATCC 17965
*Microbacterium ammoniaphilum* ATCC 15354 or a mutant thereof.

7. The composite plasmid of claim 2, which is pAJ 655.

8. The composite plasmid of claim 2, which is pAJ 611.

9. The composite plasmid of claim 2, which is pAJ 1844.

10. The composite plasmid of claim 2, which is pAJ 440.

11. The composite plasmid of claim 2, which is pAJ 3148.

12. The composite plasmid of any of claims 1 or 2, which carries in addition a gene or genes foreign to the *Coryneform glutamic* acid-producing bacterium.

13. The composite plasmid of any of claims 1 or 2, which carries in addition a gene or genes from chromosome, plasmid or phage DNA of *Coryneform glutamic* acid-producing bacterium.

14. A *Coryneform glutamic* acid-producing bacterium containing the composite plasmid of claims 1 or 2.

15. A *Escherichia coli* or *Bacillus subtilis* bacterium containing the composite plasmid of claims 1 or 2.

16. The *Coryneform glutamic* acid-producing bacterium of claim 14, wherein the bacterium is selected from the group consisting of *Brevibacterium divaricatum, Brevibacterium immariophilum, Brevibacterium lactofermentum, Brevibacterium roseum, Brevibacterium thiogenitalis, Corynebacterium acetoglutamicum, Corynebacterium callunae, Corynebacterium glutamicum, Corynebacterium lilium, Corynebacterium melassecola* and *Microbacterium ammoniaphilium.*

17. The *Coryneform glutamic* acid producing bacterium of claims 14 or 16, wherein the bacterium is a mutant having a lower activity of restriction enzyme.

18. A *Coryneform glutamic* acid-producing bacterium containing the composite plasmid of claims 12 or 13.

* * * * *